US012721678B2

(12) United States Patent
Batchelor et al.

(10) Patent No.: US 12,721,678 B2
(45) Date of Patent: Sep. 1, 2026

(54) STRUCTURED ELECTRODE FOR VAPOR POCKET IGNITION

(71) Applicant: GYRUS ACMI, INC., Westborough, MA (US)

(72) Inventors: Kester Julian Batchelor, Mound, MN (US); Teo Heng Jimmy Yang, Heath (GB)

(73) Assignee: Gyrus ACMI, Inc., Westborough, MA (US)

( * ) Notice: Subject to any disclaimer, the term of this patent is extended or adjusted under 35 U.S.C. 154(b) by 294 days.

(21) Appl. No.: 18/263,508

(22) PCT Filed: Feb. 2, 2022

(86) PCT No.: PCT/US2022/070481
§ 371 (c)(1),
(2) Date: Jul. 28, 2023

(87) PCT Pub. No.: WO2022/170321
PCT Pub. Date: Aug. 11, 2022

(65) Prior Publication Data

US 2024/0115317 A1 Apr. 11, 2024

Related U.S. Application Data

(60) Provisional application No. 63/145,037, filed on Feb. 3, 2021.

(51) Int. Cl.
*A61B 18/14* (2006.01)
*A61B 18/16* (2006.01)
(Continued)

(52) U.S. Cl.
CPC .... *A61B 18/16* (2013.01); *A61B 2017/00938* (2013.01); *A61B 2018/00083* (2013.01);
(Continued)

(58) Field of Classification Search
CPC ............. A61B 18/1206; A61B 18/148; A61B 18/1482; A61B 18/1486; A61B 18/16;
(Continued)

(56) References Cited

U.S. PATENT DOCUMENTS 4,706,667 A 11/1987 Roos
5,169,397 A 12/1992 Sakashita et al.
(Continued)

FOREIGN PATENT DOCUMENTS

CN 105050637 11/2015
CN 117320648 12/2023
(Continued)

OTHER PUBLICATIONS

"International Application Serial No. PCT/US2022/70481, International Search Report mailed May 10, 2022", 5 pgs.
(Continued)

*Primary Examiner* — Michael F Peffley
(74) *Attorney, Agent, or Firm* — Schwegman Lundberg & Woessner, P.A.

(57) ABSTRACT

An electrosurgery device can include a return electrode, an active electrode including a hydrophobic or superhydrophobic surface configured to retain a portion of gas from a vapor pocket hereon when the active electrode is in a conductive liquid solution and the active electrode has transitioned into an inactive state, and an electrically insulating material situated between the active and return electrodes.

19 Claims, 7 Drawing Sheets

(51) Int. Cl.
*A61B 17/00* (2006.01)
*A61B 18/00* (2006.01)

(52) U.S. Cl.
CPC ............... *A61B 2018/00577* (2013.01); *A61B 2018/00595* (2013.01); *A61B 2018/00625* (2013.01); *A61B 2018/00702* (2013.01)

(58) Field of Classification Search
CPC A61B 2017/00938; A61B 2018/00083; A61B 2018/00107; A61B 2018/00136; A61B 2018/00327; A61B 2018/00547; A61B 2018/00577; A61B 2018/00595; A61B 2018/00625; A61B 2018/00702; A61B 2018/1253; A61B 2018/126; A61B 2018/1472; A61B 2018/162
See application file for complete search history.

(56) References Cited

U.S. PATENT DOCUMENTS

| | | | | |
|---|---|---|---|---|
| 5,618,392 | A | 4/1997 | Furuya | |
| 5,944,715 | A | 8/1999 | Goble et al. | |
| 6,923,757 | B2 | 8/2005 | Abe et al. | |
| 2005/0283149 | A1 | 12/2005 | Thorne et al. | |
| 2006/0058583 | A1 | 3/2006 | Matsumoto et al. | |
| 2006/0241587 | A1* | 10/2006 | Heim ................. | A61B 18/1402 606/50 |
| 2007/0005060 | A1 | 1/2007 | Heim et al. | |
| 2008/0221390 | A1 | 9/2008 | Bob | |
| 2009/0030280 | A1 | 1/2009 | Matsumoto et al. | |
| 2013/0116682 | A1 | 5/2013 | Koo et al. | |
| 2014/0276407 | A1* | 9/2014 | DeVries ................. | A61B 18/16 604/103.08 |
| 2015/0366462 | A1 | 12/2015 | Ramos et al. | |
| 2017/0014111 | A1* | 1/2017 | Hulseman .............. | A61B 17/00 |
| 2019/0021786 | A1* | 1/2019 | Ward ................... | A61B 18/149 |
| 2021/0321861 | A1 | 10/2021 | Mcweeney et al. | |

FOREIGN PATENT DOCUMENTS

| | | | |
|---|---|---|---|
| DE | 112022000926 | | 11/2023 |
| JP | H0564661 | A | 3/1993 |
| JP | 2706507 | B2 | 10/1997 |
| JP | H1025427 | | 1/1998 |
| JP | 2971490 | B2 | 11/1999 |
| JP | 2000502275 | | 2/2000 |
| JP | 2000506405 | | 5/2000 |
| JP | 3469770 | B2 | 11/2003 |
| JP | 2010014468 | | 1/2010 |
| JP | 2012509140 | | 4/2012 |
| JP | 2012519224 | | 8/2012 |
| JP | 2016501723 | | 1/2016 |
| JP | 2020122991 | | 8/2020 |
| JP | 7685601 | B2 | 5/2025 |
| WO | 2010099254 | | 9/2010 |
| WO | 2016160803 | | 10/2016 |
| WO | WO-2022170321 | A1 | 8/2022 |

OTHER PUBLICATIONS

"International Application Serial No. PCT/US2022/70481, Written Opinion mailed May 10, 2022", 9 pgs.
"Japanese Application Serial No. 2023-547119, Notification of Reasons for Rejection mailed Jun. 24, 2024", W English Translation, 19 pgs.
"Chinese Application Serial No. 202280013056.3, Notification to Make Rectification (210302) mailed Sep. 21, 2023", with machine translation, 2 pgs.
"Chinese Application Serial No. 202280013056.3, Response filed Nov. 20, 2023 to Notification to Make Rectification (210302) mailed Sep. 21, 2023", with machine translation, 7 pgs.
"International Application Serial No. PCT/US2022/070481, International Preliminary Report on Patentability mailed Aug. 17, 2023", 11 pgs.
"Japanese Application Serial No. 2023-547119, Response filed Dec. 23, 24 to Notification of Reasons for Rejection mailed Jun. 24, 2024", w/ english claims, 12 pgs.
"Chinese Application Serial No. 202280013056.3, Office Action mailed Mar. 17, 2026", W English Translation, 22 pgs.

* cited by examiner 500
220
550
218
554
230
"6/7"
"6/7"

500A
220
550
554
662
554
660
222
224
230
220

500B
220
550
770
772
224
220
222
770
660
662
550

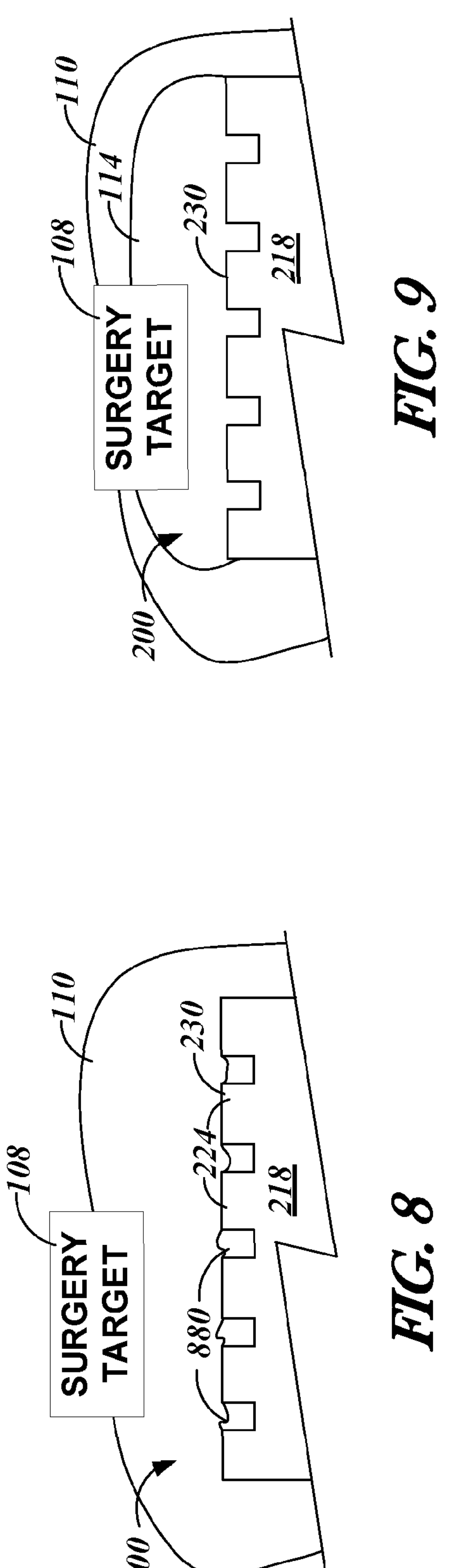
FIG. 9
FIG. 8
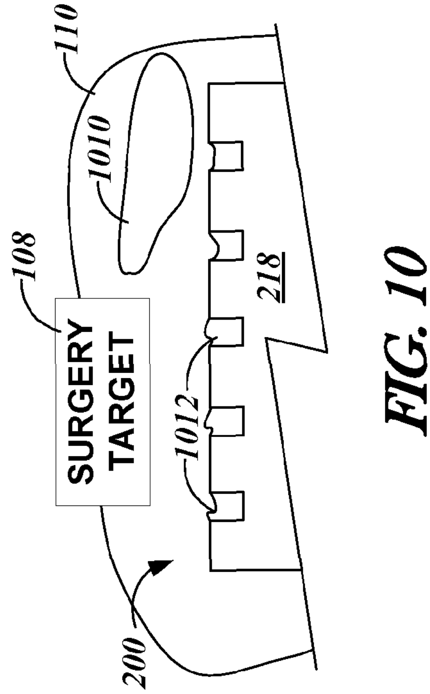
FIG. 10

1100

STRUCTURED ELECTRODE FOR VAPOR POCKET IGNITION

RELATED APPLICATIONS

This application is a U.S. national stage filing under 35 U.S.C. § 371 from International Application No. PCT/US2022/070481, filed on Feb. 2, 2022, and published as WO2022/170321 on Aug. 11, 2022, which claims the benefit of priority to U.S. Provisional Patent Application No. 63/145,037, titled "Structured Electrode for Vapor Pocket Ignition" and filed on Feb. 3, 2021, which applications and publication are hereby incorporated herein by reference in its their entirety.

FIELD

These teachings regard electrode configurations for reducing power required to generate a vapor pocket, such as for tissue vaporization.

BACKGROUND

Some electrosurgical devices vaporize tissue by creating a gas pocket in a fluid. The gas pocket can be created between an active and return electrode. The active electrode can be part of the electrosurgical device. The return electrode can be part of the electrosurgical device or can include a pad situated as a ground pad on a patient.

More particularly, some electrosurgical devices can activate in a saline environment. These electrosurgical devices apply electrical current, which causes the fluid around the active electrode to boil. The boiling causes a vapor pocket to form. That vapor pocket is used to vaporize tissue. Any tissue that comes into contact with the vapor pocket is vaporized. As electrodes get larger, the vapor pocket is larger, and more tissue can be vaporized at once.

SUMMARY

The present teachings regard improvements to electrosurgical devices. The teachings can reduce an amount of power required to establish a vapor pocket. The teachings can provide an electrosurgical device with a larger electrode than was previously possible. The teachings can provide an electrosurgical device that consumes less electrical power as compared to other electrosurgical devices without one or more of the improvements.

An electrosurgical device can include a return electrode and an active electrode. The active electrode can include a first hydrophobic surface to retain some gas from a vapor pocket while the active electrode is submerged in liquid. The electrosurgical device can include an electrically insulating material situated between the active and return electrodes.

The first hydrophobic or superhydrophobic surface can be textured to inhibit a liquid from entering spaces between protrusions of the first hydrophobic surface and allow the gas to be retained in the spaces. The active electrode can include a hydrophobic coating. The first hydrophobic surface can be mechanically, optically, or chemically etched. The first hydrophobic surface includes trenches formed in a surface thereof.

The material can include a second superhydrophobic surface. The second hydrophobic surface can be textured to inhibit a liquid from entering spaces between protrusions of the textured surface and allow the gas to be retained in the spaces. The material can include a superhydrophobic coating.

A method for bipolar electrosurgical device operation in a liquid environment can include providing electricity to an electrode in liquid to cause a vapor pocket to form and retaining some gas from the vapor pocket at a hydrophobic surface of the electrosurgical device after partial dissipation of the vapor pocket. The superhydrophobic surface can include texturing, including raised portions and recesses. Retaining the gas can include retaining the gas in one or more of the recesses.

The method can further include, after causing the vapor pocket to be formed, reducing an amount of energy (e.g., electrical energy, ultrasonic energy, or the like) provided to the electrode, such as, for example, radio frequency (RF) energy. The reduction in RF energy can be to a power sufficient to retain the vapor pocket and an electrical path between the electrode and a surgery target.

The superhydrophobic surface can be on or integrally formed with the electrode. The hydrophobic surface can be on or integrally formed with a dielectric material situated between the electrode and a return electrode.

An electrosurgery device can include a return electrode, an active electrode including a superhydrophobic surface configured to retain a gas thereon when the active electrode is in a conductive liquid solution (e.g., physiological saline) and the active electrode has transitioned into an inactive state, and an electrically insulating material situated between the active and return electrodes. The material can include a superhydrophobic surface configured to retain the gas thereon. The active electrode and the material can both include a superhydrophobic surface configured to retain the gas thereon.

The superhydrophobic surface can be integrally formed into the active electrode. The superhydrophobic surface can be textured to inhibit a liquid from entering spaces between protrusions of the textured surface and allow the gas to be retained in the spaces. The hydrophobic surface can be coated onto the active electrode.

BRIEF DESCRIPTION OF THE DRAWINGS

FIGS. 8, 9, and 10 illustrate, by way of example, an exploded view diagram of a portion of the system of FIGS. 3 and 4 in different operating states.

DETAILED DESCRIPTION

Figure 1:
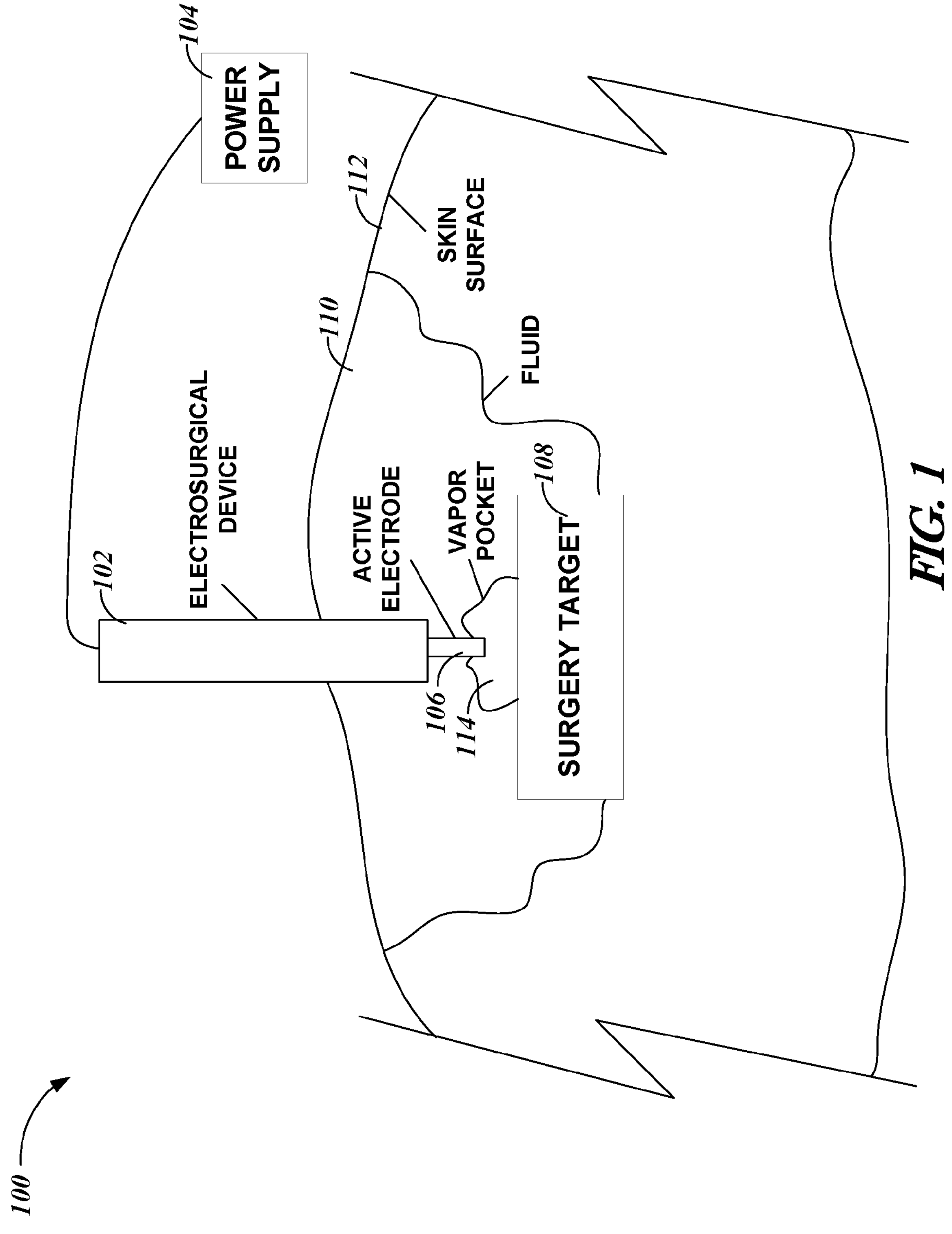
FIG. 1 illustrates, by way of example, a diagram of an embodiment of a system for ablating tissue.

A fluid, such as physiologic saline, can be introduced into a patient cavity, such as to distend the cavity. The distension of the cavity can increase an amount of space in the cavity, thus providing more room to perform surgery. An electrosurgical device can be situated in the fluid that was introduced into the patient cavity. The electrosurgical device can surgically alter tissue in the cavity through a vapor pocket. To alter (e.g., cauterize, ablate, remove, or the like) the tissue, the electrosurgical device can form a vapor pocket in the fluid. The electrosurgical device can retain the vapor pocket while consuming less power than is used in generating the vapor pocket. However, the vapor pocket can dissipate and the space consumed by the vapor pocket can be consumed by the fluid. Then, to alter further tissue, the vapor pocket can be re-established.

The power or energy consumed in establishing the vapor pocket can be prohibitively high. Surgical standards dictate that a limited amount of wattage can be applied to a patient at a given point in time and on average. The limit is currently about 300 Watts, about 400 Watts, or the like. This power limit restrains the size of the electrode. A smaller electrode can establish the vapor pocket with lower energy (e.g., RF or ultrasonic energy) than a larger electrode. The vapor pocket generated by the smaller electrode is smaller than the vapor pocket generated by the larger electrode. The power and size of the vapor pocket limits control the amount of tissue that can be altered per unit time.

To help the electrosurgical device establish a vapor pocket, a gas (e.g., air or vapor from fluid boiling) can be retained on a surface of the electrosurgical device. The retained gas can form the beginning of a vapor pocket. The retained gas can reduce an amount of power required to establish (or re-establish) the vapor pocket in the fluid. This reduction in power allows for a larger electrode that does not violate the previously discussed surgical standards while still allowing for an increase in an amount of tissue that can be ablated or vaporized per unit time. This reduction in power can allow medical personnel to operate for longer, continuous durations of time without violating the surgical standards.

The gas can be trapped using a structured surface, for example, that is hydrophobic or superhydrophobic. The structure can be configured to provide a Cassie's state. With Cassie's state, fluid is prevented from entering spaces between protrusions on a surface. With Cassie's state, a lower contact angle hysteresis, as compared to Wenzel's state, is realized. Thus, after a vapor pocket is created, and is dissipated (gets "knocked off of the active electrode"), becoming a bubble floating in the fluid, not all of that vapor pocket gets knocked off the active electrode. Instead, some of the vapor pocket is retained at the hydrophobic or superhydrophobic surface of the active electrode, other surface of the electrosurgical device, or a combination thereof. The surface structure configured in a Cassie's state can then help reduce an amount of power required to re-establish the vapor pocket and continue altering the tissue.

Making it easier to establish the vapor pocket can help reduce the power consumed in establishing the vapor pocket. In performing the tissue alteration with the electrosurgical device, the vapor pockets can get knocked off and be re-created often. Establishing the vapor pocket after it is knocked off consumes a lot of energy relative to other operation of the electrosurgical device, such as retaining the vapor pocket after creation. Using the structured surface can allow a larger electrode, and thus greater/faster tissue removal, without expending more energy than is consumed using current electrosurgical devices to initiate the next vapor pocket.

There are a variety of ways to make a surface hydrophobic or superhydrophobic. One way to make a surface superhydrophobic includes patterning the surface using an optical, chemical, or mechanical etching tool. An alternative way to make the surface hydrophobic or superhydrophobic includes molding the electrode to be hydrophobic or superhydrophobic. The etching tool can form trenches, ridges, pillars, pores, protrusions, or the like in the surface. The material that is not etched can form protrusions extending from a bottom of the trenches. The protrusions can form pillars. Sidewalls of the pillars can be defined by the trenches. The spaces between the protrusions can hold gas when the electrosurgical device is situated in fluid. The geometry, spacing, or material of the protrusions can prevent the fluid from entering the trenches.

There are many examples of hydrophobic and superhydrophobic surfaces. Example dimensions of a textured surface that includes pillars separated by spaces are provided. The pillars can include a height of a few nanometers tall (e.g., about 2 nm) to about 20 nm tall. The pillars can be on the order of a few nanometers to tens or hundreds of nanometers wide (e.g., from about 50 nm to about 300 nm wide). A center-to-center distance of the pillars can be about 120 nm to about 350 nm. A coating that include the pillars and spaces can be from about 20 nm to about 200 nm thick. This is merely an example of dimensions; other dimensions are possible.

Another way of making a surface superhydrophobic includes coating the surface with a superhydrophobic material. Such materials are typically not as conductive as the electrode and can interfere with conductivity. Further, such materials can be adversely affected by electrical current of the magnitude generated by the electrosurgical device. Thus, the surface etched to be superhydrophobic and the surface with the superhydrophobic coating are structurally different and operate with different electrical characteristics.

FIG. 1 illustrates, by way of example, a diagram of an embodiment of a system 100 for surgically altering tissue. The system 100 as illustrated includes an electrosurgical device 102 and a power supply 104. The electrosurgical device 102 can include or use an endoscope, laparoscope, arthroscope, or a dedicated cautery or ablation tool, or a minimally-invasive device or the like. The electrosurgical device 102 as illustrated includes a monopolar electrode 106 for cautery, ablation, vaporization, or the like, of a surgery target 108. FIG. 1 depicts a monopolar arrangement but a bipolar arrangement or other arrangement could be used. A region around the surgery target 108 can be at least partially filled with a conductive fluid 110, such as physiologic saline, glycine, or the like. The surgery target 108 can be internal to a patient and can be accessed through a natural or manmade orifice, such as a hole through skin or other tissue 112 of the patient. The tissue 112 can include a prostate area flooded with saline, a tonsil area, tissue around a pocket in a knee, elbow, leg, arm, torso, head, neck, or other portion of an animal.

The electrosurgical device 102 can be used for dissection, resection, vaporization, desiccation, coagulation or a combination thereof. Example urologic surgeries that can be performed using the electrosurgical device include urethroscopy, cystoscopy, ureteroscopy, nephoscopy, and percutaneous surgery. Examples of liquid immersed surgeries in gynecology include transcervical or hysteroscopic procedures to remove myomas. Urological procedures may include electro-vaporization of the prostate gland (EVAP) (sometimes called transurethral vaporization of the prostate (TUVP)), transurethral resection of the prostate (TURP), interstitial ablation of the prostate gland by a percutaneous or periurethral route, transurethral or percutaneous resection of urinary tract tumors, division of strictures, ureter, ureteral orifice, bladder neck or urethra, correction ofureterocele, shrinkage of bladder diverticular, cystoplasty procedures, thermally induced shrinkage of the pelvic floor, excision of diseased tissue, hemostasis, or a combination thereof. Examples of arthroscopic surgeries include meniscectomy of the knee joint, lateral retinacular release of the knee joint, removal of anterior or posterior cruciate ligaments or remnants thereof, labral tear resection, acromioplasty, bursectomy and subacromial decompression of the shoulder joint, anterior release of the temporomandibular joint, synovectomy, cartilage debridement, chondroplasty, division of intra-articular adhesions, fracture and tendon debridement, inducing thermal shrinkage of joint capsules, subluxation to any articulated joint of the body, discectomy of a disc prolapse or as part of a spinal fusion, excision of diseased tissue, hemostasis, or a combination thereof.

The electrosurgical device 102, in an active state, can vaporize a portion of the fluid 110. The vaporization of the fluid 110 can form a vapor pocket 114 in the fluid 110. When the vapor pocket 114 extends between the electrode 106 and the surgery target 108, electricity can flow from the electrode 106 to the surgery target 108. The electricity incident on the surgery target 108 can ablate, cauterize, or otherwise alter the surgery target 108. The result can be removal, hardening, or closure of the surgery target 108, for example.

More power is used to generate the vapor pocket 114 than is required to alter the surgery target 108 and maintain the vapor pocket 114. A spike of electricity from the power supply 104 can help generate the vapor pocket 114. Then the electricity from the power supply 104 can be reduced to a level that maintains the vapor pocket 114 and alters the surgery target 108. This reduction in electricity can allow the electrode 106 to be made larger or the surgery to last longer without violating the surgical standards.

At some point, however, the vapor pocket 114 will collapse. The vapor pocket 114 collapse can be due to the electricity from the power supply 104 being reduced below a threshold required to maintain the vapor pocket 114, the active electrode 106 moving too far away from the surgery target 108, fluid intrusion into the vapor pocket 114, among others. To continue altering the surgery target 108, the electrical power from the power supply 104 can be increased to re-establish the vapor pocket 114.

To reduce the electrical power required to establish and re-establish the vapor pocket 114, the active electrode 106 can be configured to trap a portion of the vapor pocket 114 on a surface thereof. To trap the portion of the vapor pocket 114, the active electrode 106 can include a hydrophobic or superhydrophobic surface (referred to as a "vapor retaining surface"). The vapor retaining surface can prohibit the fluid 110 from penetrating into spaces between protrusions of the vapor retaining surface. This leaves a portion of the vapor pocket 114 in the spaces. By trapping this portion of the vapor pocket 114, the volume of fluid 110 to be vaporized for altering the surgery target 108 can be reduced. This is because there is a volume of the vapor pocket 114 that persists on the surface of the electrode 106, other vapor retaining surface of the electrosurgical device 102, or a combination thereof.

Figure 2:
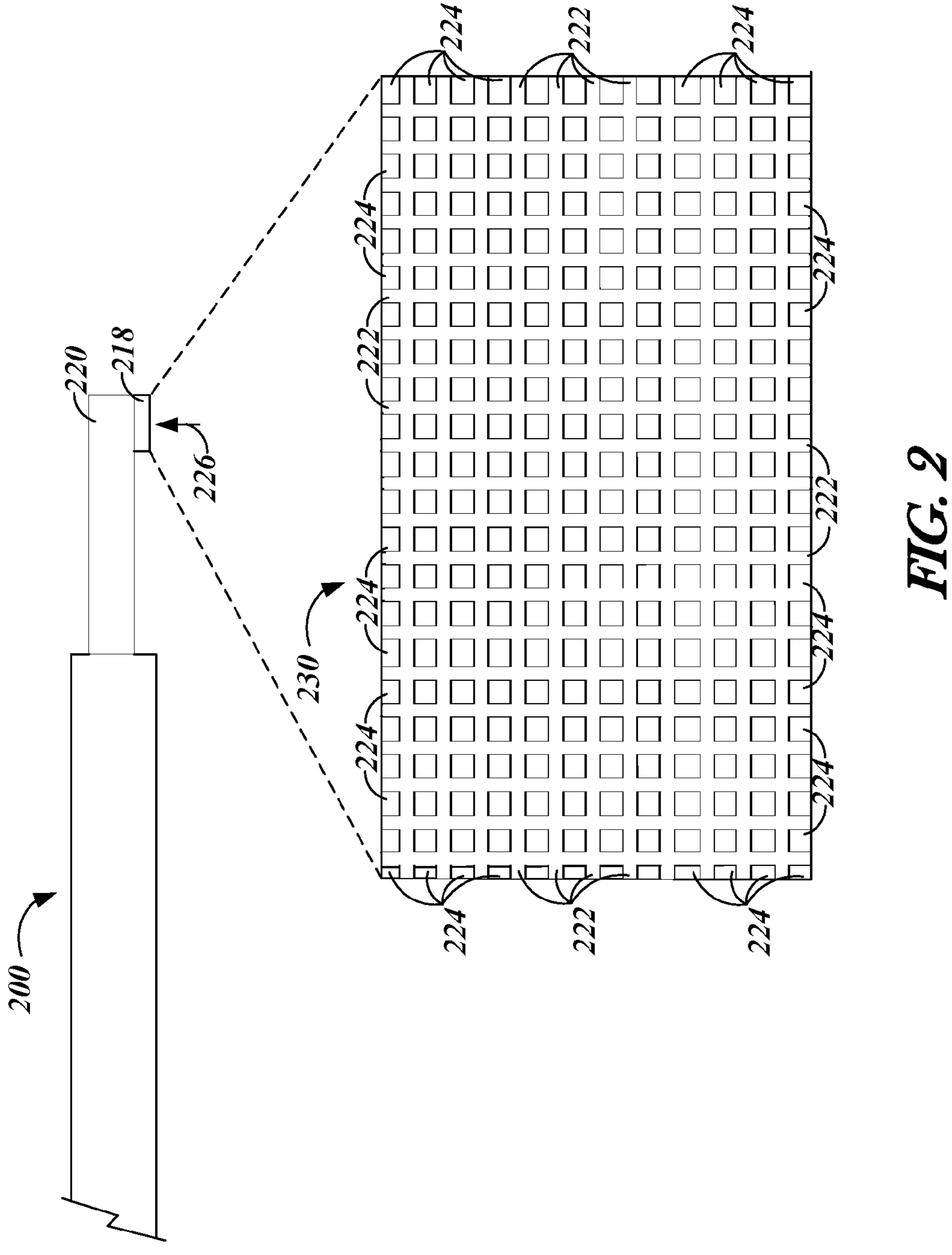
FIG. 2 illustrates, by way of example, a diagram of an electrosurgical device and an exploded view of a vapor retaining surface.

FIG. 2 illustrates, by way of example, a diagram of an electrosurgical device 200 and an exploded view of a vapor retaining surface 230. The exploded view is from a perspective indicated by arrow 226. The electrosurgical device 200 of FIG. 2 is a bipolar device but could be monopolar. The electrosurgical device 200 includes an active electrode 218 and a return electrode 220. The active electrode 218 can include the surface from which electricity from the electrical supply 104 (see FIG. 1) exits the electrosurgical device 200 towards the surgery target 108 (see FIG. 1). The return electrode 220 completes the electrical path for electricity to travel back to the power supply 104. The return electrode 220 can be electrically coupled to electrical ground.

The vapor retaining surface 230 as illustrated includes protrusions 224. The vapor retaining surface 230 further includes spaces 222 between the protrusions 224. The spaces 222 can be contiguous, such as to form one or more channels, trenches, indents, or the like between the protrusions 224. In the example of FIG. 2, the spaces 222 are contiguous and form one channel between all the protrusions 224.

A distance between the protrusions 224 can be controlled, such as to reduce the chances the fluid 110 (see FIG. 1) enters the spaces 222. Likewise, a shape of the protrusions 224 can be controlled to reduce the chances the fluid 110 enters the spaces 222. The distance between and shape of the protrusions 224 helps control a contact angle between the surface 230 and the fluid 110.

The vapor retaining surface 230 can be integrally formed with or a coating added to the electrosurgical device 200. Integrally forming the vapor retaining surface 230 can include optically, chemically, or mechanically etching the electrosurgical device 200 to form the protrusions 224 and spaces 222. Coating the vapor retaining surface 230 onto the electrosurgical device 200 can include forming or otherwise retaining the vapor retaining surface 230 and adhering the vapor retaining surface 230 on the electrosurgical device 200.

Since the coating is very likely formed of a different material than the portion of the electrosurgical device 200 that is etched, the etched vapor retaining surface can have different operating characteristics than a coated vapor retaining surface. For example, the etched vapor retaining surface can have a longer operational lifespan than the coated vapor retaining surface (assuming a same electrical power). The operational lifespan in this instance is the amount of time before degrading beyond the ability to establish or maintain the vapor pocket 114.

While FIG. 2 illustrates the vapor retaining surface 230 as part of the active electrode 218, the vapor retaining surface 230 can additionally or alternatively be a part of a dielectric that separates the active electrode 218 and the return electrode 220, the return electrode 220, other portion of the electrosurgical device 200 proximate the vapor pocket 114, or a combination thereof.

Figure 3:
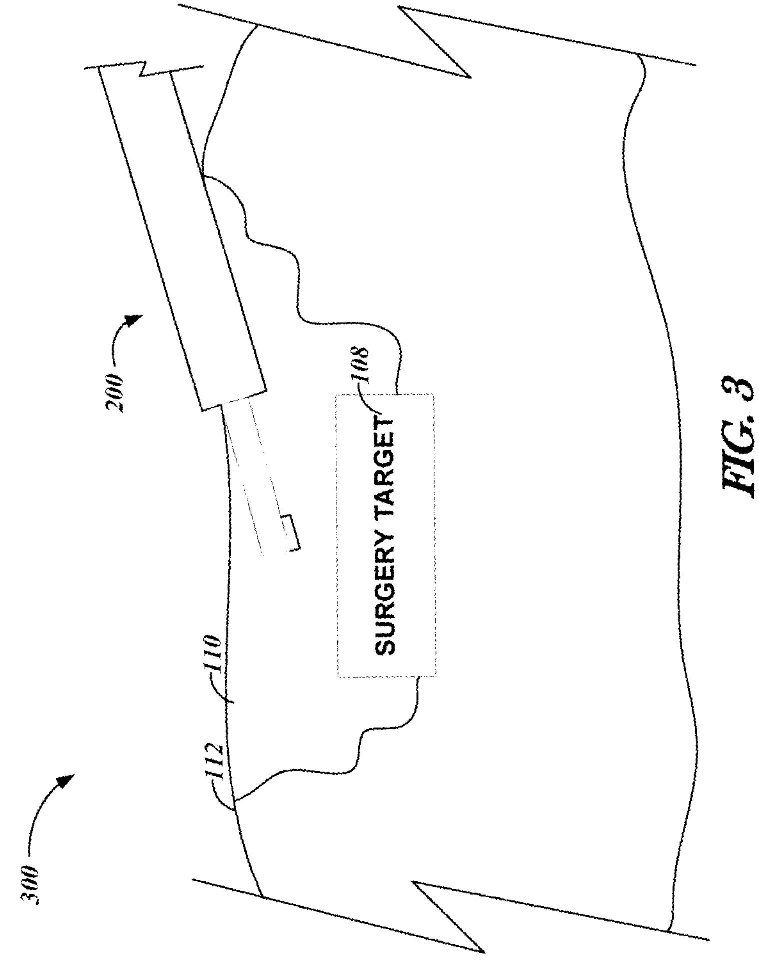
FIG. 3 illustrates, by way of example, a diagram of an embodiment of a system for altering a surgery target.

FIG. 3 illustrates, by way of example, a diagram of an embodiment of a system 300 for altering the surgery target 108. The system 300 includes the electrosurgical device 200 approaching the surgery target 108. Typically, a physician or other medical personnel, advances the electrosurgical device 200 towards the surgery target 108. The personnel can push the electrosurgical device 200 through a natural or manmade orifice through the tissue 112, towards the surgery target 108. The view provided in FIG. 3 is before electricity is provided to the electrosurgical device 200. When the electrosurgical device 200 is sufficiently close to the surgery target 108, the personnel can cause electricity (e.g., from the power supply 104, see FIG. 1) to be provided to the electrosurgical device 200. Sufficiently close in this context means close enough to cause electricity to flow from the electrosurgical device 200 to the surgery target 108 after forming the vapor pocket 114.

Figure 4:
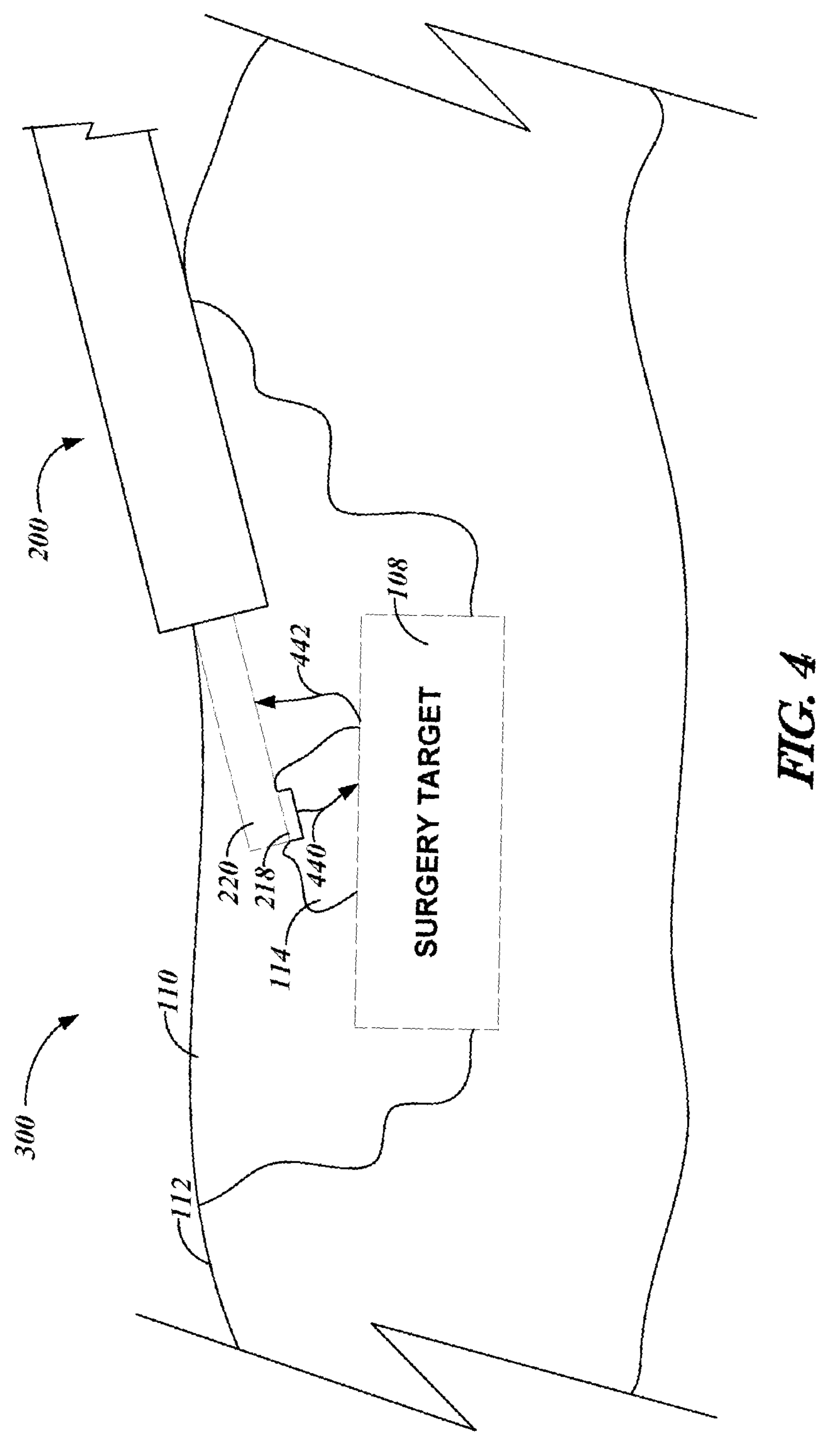
FIG. 4 illustrates, by way of example, a diagram of an embodiment of the system of FIG. 3 after electricity is supplied to the electrosurgical device.

FIG. 4 illustrates, by way of example, a diagram of an embodiment of the system 300 of FIG. 3 after electricity is supplied to the electrosurgical device 200. The electricity, when of sufficient power, causes the fluid 110 to boil and vaporize proximate the active electrode 218. Electricity from the active electrode 218 can then flow to the surgery target 108 (indicated by arrow 440) through the vapor pocket 114. The electricity incident on surgery target 108 can cauterize, cut, ablate, or otherwise alter the surgery target 108. Electricity can flow from the surgery target 108, through the fluid 110, to the return electrode 220.

Eventually, the electrosurgical device 200 will provide electricity of insufficient power to retain the vapor pocket 114. This can be due to the personnel operating the electrosurgical device 200 stopping or reducing the electricity, fluid 110 interfering with the vapor pocket 114, degradation of the active electrode 218 or a vapor retaining surface 230 coating thereon, or the like. To re-establish the vapor pocket 114, the personnel can re-initiate electricity to the electrosurgical device 200, such as by pressing a button, switch, or the like on the electrosurgical device 200 that closes an electrical circuit connected to the electrical power supply 104.

A portion of the vapor pocket 114 can be retained by the vapor retaining surface 230. Retaining the portion of the vapor pocket 114 can reduce a volume of the fluid 110 to be vaporized in facilitating the electrical path to the surgery target 108. Reducing the volume of the fluid 110 to be vaporized can reduce an electrical power required to generate a next vapor pocket, reduce an amount of time the electrical power is greater than required for ablation, cautery, or the like, or a combination thereof. Reducing the volume of the fluid 110 to be vaporized or the amount of time the electrical power is greater than required for altering the surgery target 108 reduces an amount of electrical power (on average) to alter the surgery target 108. The reduction in electrical power required to generate the vapor pocket 114 allows the power to be increased at a different time during a procedure without violating the surgical standards of power provided to tissue. The reduction in electrical power required to generate the vapor pocket 114 can allow for a larger active electrode to be operated below the surgical standards. This larger active electrode can allow personnel to remove more tissue in less time than is possible with a smaller active electrode or an electrode that does not include the vapor retaining surface 230.

Figures 5, 6, 7:
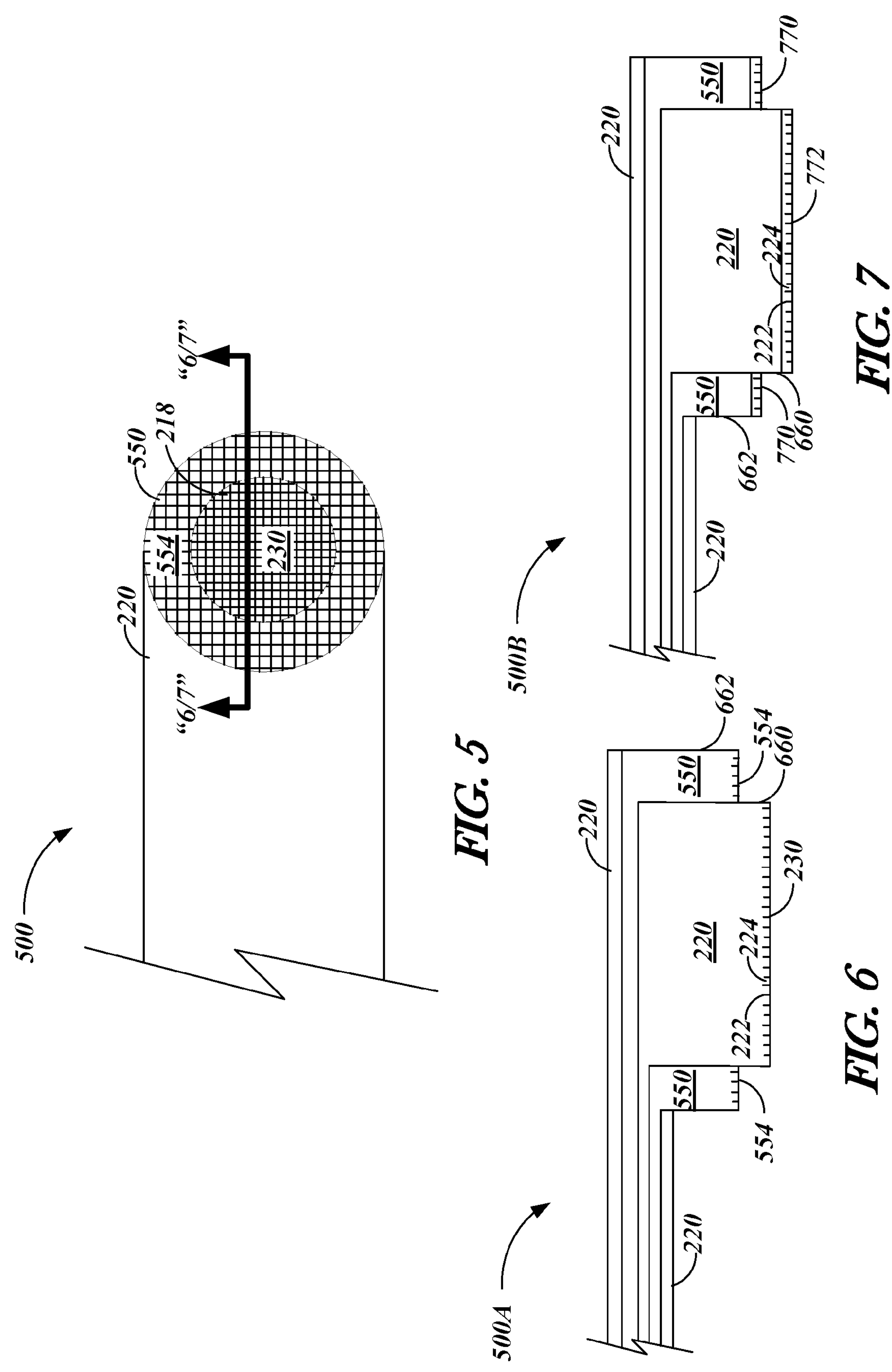
FIG. 5 illustrates, by way of example, a diagram of an embodiment of an electrosurgical device.
FIG. 6 illustrates, by way of example, a cross-section diagram of an embodiment of the electrosurgical device from the perspective of the arrows labelled "6/7" in FIG. 5.
FIG. 7 illustrates, by way of example, a cross-section diagram of another embodiment of the electrosurgical device from the perspective of the arrows labelled "6/7" in FIG. 5.

FIG. 5 illustrates, by way of example, a diagram of an embodiment of an electrosurgical device 500. The electrosurgical device 500 includes the active electrode 218 with a first vapor retaining surface 230. The vapor retaining surface 230 can face the surgery target 108 when in normal use. The electrosurgical device 500 further includes a dielectric material 550 with a second vapor retaining surface 554. The dielectric material 550 can include an electrically insulating material. The dielectric material 550 can prevent the active electrode 218 from shorting with the return electrode 220. The dielectric material 550 can include any electrically isolating material that can be safely used within the body, such as, for example, ceramic, or more particular representative embodiments including alumina oxide ($Al_2O_3$), Zirconia Toughened Alumina (ZTA), silicon nitride, non-carbon tracking high-temperature polymer (e.g., nylon, polyamide, polytetrafluoroethane (PTFE), ethylenetetrafluoroethylene (ETFE), silicon, silicon rubber, or the like.

One or more of the first vapor retaining surface 230 and second vapor retaining surface 554 can be etched into or coated onto the electrosurgical device 500. The first vapor retaining surface 230 can be etched and the second vapor retaining surface 554 can be coated, or vice versa.

In the example of FIG. 5, the return electrode 220 is not coated or etched to include a vapor retaining surface. This can make the return electrode 220 appear as a bigger surface than the active electrode 218 when submerged in the fluid 110 and during ignition (electricity application to the active electrode 218). This can help dictate which electrode becomes the active electrode and which electrode becomes the return electrode after power is supplied from the power supply 104 (see FIG. 1). Typically, the electrode with less surface area becomes the active electrode and the electrode with a greater surface area becomes the return electrode. If the return electrode 220 is etched or coated to include a vapor retaining surface, the surface area in contact with the conductive fluid 110 can be reduced as the fluid 110 is displaced by vapor retained at the surface. Thus, not coating or etching the return electrode 220 to include the vapor retaining surface can help dictate which electrode is active and which is passive before power is applied.

FIG. 6 illustrates, by way of example, a cross-section diagram of an embodiment of the electrosurgical device 500A from the perspective of the arrows labelled "6/7" in FIG. 5. The electrosurgical device 500A includes first and second vapor retaining surfaces 230, 554 etched into the active electrode 218 and the dielectric material 550, respectively. The return electrode 220 in the embodiment of FIG. 6 does not include a vapor retaining surface but could also be etched or coated to include a third vapor retaining surface. While the active electrode 218 is illustrated as extending beyond a perimeter of the dielectric material 550, this is not always the case. The active electrode 218, in some embodiments can be within or otherwise not extend beyond the perimeter of the dielectric material 550.

FIG. 7 illustrates, by way of example, a cross-section diagram of another embodiment of the electrosurgical device 500B from the perspective of the arrows labelled "6/7" in FIG. 5. The electrosurgical device 500B includes first and second vapor retaining surface coatings 772, 770 applied to the active electrode 218 and the dielectric material 550, respectively. The vapor retaining surface coatings 772, 770 can include a structure that prevents liquid from infiltrating the spaces between pillars of the vapor retaining surface coatings 772, 770. The vapor retaining surface coatings 772, 770 can be configured in a Cassie's state where liquid rests upon the protrusions and does not infiltrate the spaces between the pillars, which includes representative compounds such as, for example, silane, siloxane, polysiloxane, fluorosiloxane, polydimethylsiloxane (PMDS, PMDSO), hexamethyldisiloxane, tetramethyldisoloxane, or the like. The dielectric material 550 can include plastic, polymer, ceramic, mica, glass, air, epoxy, resin, a combination thereof or the like.

While FIGS. 6 and 7 illustrate the active electrode 218 as including only a single vapor retaining surface 230, 554, other surfaces of the active electrode 218, such as the surface 660, can be etched or coated to be a vapor retaining surface.

Similarly, the dielectric material 550 can include another surface 662 that is etched or coated to be a vapor retaining surface.

FIGS. 8, 9, and 10 illustrate, by way of example, an exploded view diagram of a portion of the system 300 of FIGS. 3 and 4 in different operating states. The state in FIG. 8 is during insertion of the electrosurgical device 200 into the patient, such as before the electrosurgical device 200 has been powered on. The electrode 218 is configured with the vapor retaining surface 230. Thus, when the electrosurgical device 200 is inserted into the fluid 110, the fluid 110 does not penetrate into spaces 222 between protrusions 224 of the surface 230. The surface 230 retains air 880 between the protrusions 224 as it is submerged in the fluid 110. The retained air 880 reduces a volume of the fluid 110 that is to be displaced (e.g., boiled, vaporized, converted to gas, or the like) in generating an electrical path that includes the surgery target 108.

The state in FIG. 9 is after electrical power has been provided to the electrosurgical device 200. The electrical power provided causes a portion of the fluid 110 to displace and form a vapor pocket 114. The vapor pocket 114 can extend between the electrosurgical device 200 and the surgery target 108. In such an active state, electricity can flow from the electrode 218, to the surgery target 108, and to a return electrode 220 (see FIG. 2 among others). The electricity can ablate, cauterize, or otherwise alter the surgery target 108. The amount of electrical power consumed in generating the vapor pocket 114 can be reduced as compared to electrosurgical devices that do not include the vapor retaining surface 230. The reduction in electrical power consumed can be due, at least in part, to the air 880 (see FIG. 8) trapped at the surface 230 before electrical power is applied to the active electrode 218. Retaining the vapor pocket 114 can consume less electrical power than generating the vapor pocket 114. The electrical power provided to the electrosurgical device 200 can thus be reduced while the electrosurgical device is in the active, pocket retention state illustrated in FIG. 9.

The state in FIG. 10 is after the vapor pocket 114 has been knocked off. Knocking off the vapor pocket 114 means a portion of the vapor pocket 114 becomes a bubble 1010 floating in the fluid 110 and another portion of the vapor pocket 114 is retained as vapor bubbles 1012 on the vapor retaining surface 230. Knocking off the vapor pocket 114 causes the electrical path between the electrode 218 and the surgery target 108 to be broken. The vapor pocket 114 can be re-established, and the electrical path between the electrosurgical device 200 and the surgery target 108 to be re-formed, such as by providing electrical power to the electrosurgical device 200 sufficient to establish the vapor pocket 114.

Figure 11:
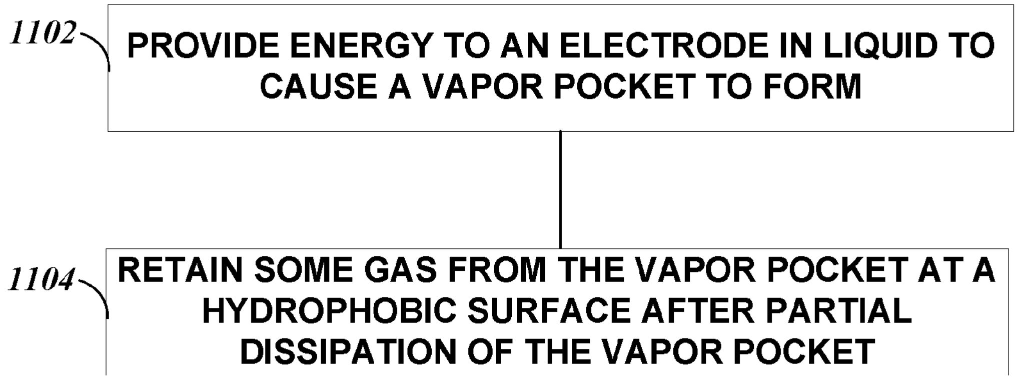
FIG. 11 illustrates, by way of example, a diagram of an embodiment of a method for operating an electrosurgical device, such as one of the electrosurgical devices discussed herein.

FIG. 11 illustrates, by way of example, a diagram of an embodiment of a method 1100 for operating an electrosurgical device, such as one of the electrosurgical devices discussed herein. A method 1100 for bipolar electrosurgical device operation in a liquid environment can include providing electricity to an electrode in liquid to cause a vapor pocket to form, at operation 1102; and retaining some gas from the vapor pocket at a hydrophobic surface of the electrosurgical device after partial dissipation of the vapor pocket, at operation 1104.

The method 1100 can further include, wherein the hydrophobic surface includes texturing including raised portions and recesses, wherein the retaining gas includes retaining gas in one or more of the recesses. The method 1100 can further include after causing the vapor pocket to be formed, reducing an amount of electricity provided to the electrode. The method 1100 can further include, wherein the reduction in electricity is to a power sufficient to retain the vapor pocket and an electrical path between the electrode and a surgery target.

The method 1100 can further include, wherein the hydrophobic surface is on or integrally formed with the electrode. The method 1100 can further include, wherein the hydrophobic surface is on or integrally formed with a dielectric material situated between the electrode and a return electrode.

The method steps disclosed herein can be performed in any order except as specified otherwise. Moreover, one or more of the method steps can be combined with other steps; can be omitted or eliminated; can be repeated; and/or can separated into individual or additional steps.

The explanations and illustrations presented herein are intended to acquaint others skilled in the art with the invention, its principles, and its practical application. The above description is intended to be illustrative and not restrictive.

Those skilled in the art may adapt and apply the teachings in its numerous forms, as may be best suited to the requirements of a particular use.

Accordingly, the embodiments of the present teachings as set forth are not intended as being exhaustive or limiting of the teachings. Further, components of the specific embodiments can be combined with components of other embodiments of the teachings. The scope of the teachings should, therefore, be determined not with reference to this description, but should instead be determined with reference to the appended claims, along with the full scope of equivalents to which such claims are entitled. The omission in the following claims of any aspect of subject matter that is disclosed herein is not a disclaimer of such subject matter, nor should it be regarded that the inventors did not consider such subject matter to be part of the disclosed inventive subject matter.

Plural elements or steps can be provided by a single integrated element or step. Alternatively, a single element or step might be divided into separate plural elements or steps. The disclosure of "a" or "one" to describe an element or step is not intended to foreclose additional elements or steps. While the terms first, second, third, etc., may be used herein to describe various elements, components, regions, layers and/or sections, these elements, components, regions, layers and/or sections should not be limited by these terms. These terms may be used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. An electrosurgical device comprising:

a return electrode;

an active electrode including a first hydrophobic or superhydrophobic surface to retain some gas from a vapor pocket while the active electrode is submerged in liquid, the first hydrophobic or superhydrophobic surface comprises protrusions extending from a surface of the active electrode and spaces between the protrusions that trap gas in the spaces between the protrusions, the protrusions configured to prevent the liquid from penetrating into the spaces and maintain the gas trapped in the spaces (i) when the active electrode is submerged in the liquid and (ii) after the active electrode transitions from an active state to an inactive state; and an electrically insulating material situated between the active and return electrodes.

2. The device of claim 1, wherein the first hydrophobic or superhydrophobic surface is textured to inhibit a liquid from entering the spaces between the protrusions of the first hydrophobic or superhydrophobic surface and allow the gas to be retained in the spaces.

3. The device of claim 2, wherein the first hydrophobic or superhydrophobic surface is configured in a Cassie's or Cassie-Baxter's state to inhibit the liquid from entering the spaces between the protrusions.

4. The device of claim 1, wherein the active electrode includes a hydrophobic or superhydrophobic coating.

5. The device of claim 1, wherein the first hydrophobic or superhydrophobic surface is mechanically etched.

6. The device of claim 1, wherein the electrically insulating material includes a second hydrophobic or superhydrophobic surface.

7. The device of claim 6, wherein the second hydrophobic or superhydrophobic surface is textured to inhibit a liquid from entering spaces between protrusions of the textured surface and allow the gas to be retained in the spaces.

8. The device of claim 6, wherein the second hydrophobic or superhydrophobic surface includes a hydrophobic or superhydrophobic coating.

9. The device of claim 1, wherein the first hydrophobic or superhydrophobic surface includes trenches formed in a surface thereof.

10. An electrosurgery device comprising:

a return electrode;

an active electrode including a hydrophobic or superhydrophobic surface configured to retain a gas thereon when the active electrode is in a conductive liquid solution and the active electrode has transitioned into an inactive state, the hydrophobic or superhydrophobic surface comprises protrusions extending from a surface of the active electrode and spaces between the protrusions that trap the gas in the spaces between the protrusions, the protrusions configured to prevent the liquid from penetrating into the spaces and maintain the gas trapped in the spaces (i) when the active electrode is submerged in the liquid and (ii) after the active electrode transitions from an active state to an inactive state; and an electrically insulating material situated between the active and return electrodes.

11. The device of claim 10, wherein the electrically insulating material includes a second hydrophobic or superhydrophobic surface configured to retain the gas thereon.

12. The device of claim 11, wherein the second hydrophobic or superhydrophobic surface includes a hydrophobic or super hydrophobic coating.

13. The device of claim 10, wherein the hydrophobic or superhydrophobic surface is integrally formed into the active electrode.

14. The device of claim 13, wherein the hydrophobic or superhydrophobic surface is textured to inhibit a liquid from entering the spaces between protrusions of the textured surface and allow the gas to be retained in the spaces.

15. The device of claim 14, wherein the hydrophobic or superhydrophobic surface is configured in a Cassie's or Cassie-Baxter's state to inhibit the liquid from entering the spaces between the protrusions.

16. The device of claim 10, wherein the hydrophobic or superhydrophobic surface is coated onto the active electrode.

17. A method for bipolar electrosurgical device operation in a liquid environment, the method comprising:

providing energy to an electrode in liquid to cause a vapor pocket to form; and retaining some gas from the vapor pocket at a hydrophobic or superhydrophobic surface of the electrosurgical device after partial dissipation of the vapor pocket, the hydrophobic or superhydrophobic surface comprises protrusions extending from a surface of the electrode and spaces between the protrusions that trap gas in the spaces between the protrusions, the protrusions configured to prevent the liquid from penetrating into the spaces and maintain the gas trapped in the spaces when the electrode is submerged in the liquid; and retaining the gas from the vapor pocket in the spaces after the electrode transitions from an active state to an inactive state.

18. The method of claim 17, wherein the hydrophobic or superhydrophobic surface is configured in a Cassie's or Cassie-Baxter's state.

19. The method of claim 17, further comprising after causing the vapor pocket to be formed, reducing an amount of energy provided to the electrode while maintaining the vapor pocket.

* * * * *